US008251939B2

(12) United States Patent
Aune et al.

(10) Patent No.: US 8,251,939 B2
(45) Date of Patent: Aug. 28, 2012

(54) CERVICAL TRACTION/STRETCH DEVICE AND METHOD FOR ITS USE

(75) Inventors: Erling Aune, Vancouver, WA (US); Nathan Chitwood, Vancouver, WA (US); Susan Nickell, Kalispell, MT (US)

(73) Assignee: International Rehabilatative Sciences, Inc., Vancouver, WA (US)

( * ) Notice: Subject to any disclaimer, the term of this patent is extended or adjusted under 35 U.S.C. 154(b) by 213 days.

(21) Appl. No.: 12/657,050

(22) Filed: Jan. 12, 2010

(65) Prior Publication Data

US 2010/0121243 A1 May 13, 2010

Related U.S. Application Data

(63) Continuation-in-part of application No. 12/069,328, filed on Feb. 8, 2008.

(51) Int. Cl.
*A61F 5/00* (2006.01)

(52) U.S. Cl. ........................................... 602/36; 602/18

(58) Field of Classification Search .................... 602/13, 602/17–19, 32–38; 601/38, 149; 5/622, 5/637, 638, 640, 644
See application file for complete search history.

(56) References Cited

U.S. PATENT DOCUMENTS

| | | | | |
|---|---|---|---|---|
| 3,343,532 A | | 9/1967 | Zumaglini | |
| 4,058,112 A | | 11/1977 | Johnson | |
| 4,099,523 A | | 7/1978 | Lowrey | |
| 4,508,109 A | | 4/1985 | Saunders | |
| 4,543,947 A | | 10/1985 | Blackstone | |
| 4,617,691 A | | 10/1986 | Monti et al. | |
| 4,702,235 A | | 10/1987 | Hong | |
| 4,771,493 A | | 9/1988 | Park | |
| 4,805,603 A | | 2/1989 | Cumberland | |
| 4,832,007 A | | 5/1989 | Davis, Jr. et al. | |
| 4,850,003 A | | 7/1989 | Huebeck et al. | |
| 5,060,661 A | | 10/1991 | Howard | |
| 5,067,483 A | | 11/1991 | Freed | |
| 5,092,322 A | | 3/1992 | Gantz | |
| 5,181,904 A | | 1/1993 | Cook et al. | |
| 5,243,722 A | | 9/1993 | Gusakov | |
| 5,382,226 A | | 1/1995 | Graham | |
| 5,403,266 A | | 4/1995 | Bragg et al. | |
| 5,441,479 A | | 8/1995 | Chitwood | |
| 5,454,781 A | | 10/1995 | Chitwood | |
| 5,569,176 A | | 10/1996 | Graham | |
| 5,575,295 A | * | 11/1996 | Khalsa et al. | 5/636 |
| 5,752,927 A | | 5/1998 | Rogachevsky | |
| 5,823,982 A | | 10/1998 | Park | |
| 5,916,185 A | * | 6/1999 | Chitwood | 602/18 |
| 6,289,538 B1 | | 9/2001 | Fidge | |
| 6,447,468 B1 | | 9/2002 | Hankins et al. | |

(Continued)

FOREIGN PATENT DOCUMENTS

KR 20020071465 A 4/2005

*Primary Examiner* — Michael A. Brown

(74) *Attorney, Agent, or Firm* — Blank Rome LLP

(57) ABSTRACT

A cervical traction/stretch system includes a traction/stretch mechanism for applying tension between a body's head and shoulders, the traction/stretch mechanism including a bellows; a pump operatively coupled with the traction/stretch mechanism for alternately inflating and deflating the bellows; and an at least semi-automatic controller operatively coupled with the pump for at least semi-automatically controlling the pump by activating and deactivating the same in such manner as to alternately and repeatably inflate and deflate the bellows to prescribed pressure levels over prescribed pressure intervals.

32 Claims, 10 Drawing Sheets

U.S. PATENT DOCUMENTS

| | | | | |
|---|---|---|---|---|
| 7,048,705 | B2 | 5/2006 | Pillai | |
| 7,070,573 | B2 | 7/2006 | Axelsson | |
| 7,507,216 | B2 * | 3/2009 | Buckman et al. | 602/32 |
| 2009/0198163 | A1 * | 8/2009 | Senyei et al. | 602/18 |
| 2009/0204046 | A1 | 8/2009 | Chitwood et al. | |
| 2010/0042026 | A1 * | 2/2010 | Kloecker et al. | 601/149 |

* cited by examiner

CERVICAL TRACTION/STRETCH DEVICE AND METHOD FOR ITS USE

RELATED APPLICATIONS

This application is a Continuation-in-Part of and claims the benefit of priority to U.S. Non-Provisional application Ser. No. 12/069,328, filed on Feb. 8, 2008 and entitled CERVICAL TRACTION/STRETCH DEVICE KIT, the contents of which are hereby incorporated herein in their entirety by this reference.

FIELD OF THE INVENTION

The invention relates generally to the field of medical equipment. More particularly, the invention relates to cervical traction devices and use methods for in-home treatment.

DESCRIPTION OF THE RELATED ART

Prior art cervical traction/stretch devices are disclosed in the following U.S. Patents:

| U.S. Pat. No. | Patentee |
|---|---|
| 3,343,532 | Zumaglini |
| 4,058,112 | Johnson |
| 4,099,523 | Lowery |
| 4,508,109 | Saunders |
| 4,543,947 | Blackstone |
| 4,617,691 | Monti et al. |
| 4,702,235 | Hong |
| 4,771,493 | Park |
| 4,805,603 | Cumberland |
| 4,832,007 | Davis Jr. et al. |
| 4,850,003 | Huebeck et al. |
| 5,060,661 | Howard |
| 5,067,483 | Freed |
| 5,181,904 | Cook et al. |
| 5,243,722 | Gusakov |
| 5,382,226 | Graham |
| 5,403,266 | Bragg et al. |
| 5,441,781 | Chitwood |
| 5,454,781 | Chitwood |
| 5,569,176 | Grahm |
| 5,752,927 | Rogachevsky |
| 5,823,982 | Park |
| 5,916,185 | Chitwood |
| 6,289,538 | Fidge |
| 6,447,468 | Hankins et al. |
| 7,048,705 | Pillai |
| 7,070,573 | Axelsson |

The most pertinent prior art patents are the Chitwood U.S. Pat. Nos. 5,441,781; 5,454,781; and 5,916,184. This application is directed to improvements to the cervical/stretch devices disclosed in these patents and to a cervical/stretch device kit including new and improved elements.

Users of cervical traction systems often are confined to a sterile and attended clinical or hospital setting in which doctors and nurses prescribe, administer, monitor, and chart the treatment or therapy session. Traction patients typically feel confined by equipment, dedicated and special-purpose beds or cots or benches, and required, e.g. typically supine, and uncomfortable poses. And of course, the patient feels the stresses of being under someone else's direction and in an unfamiliar environment. Finally, there can be performance anxiety as with any required and scrutinized, albeit voluntary, yielding of control to another. Some of the problems of such an alien environment and condition for cervical traction are addressed in the above U.S. patent application Ser. No. 12/069,328 subject to common ownership herewith by International Rehabilitative Sciences, Inc. of Vancouver, Wash., USA.

The above-referenced '328 patent application relates to a kit including a cervical traction/stretch device which is positioned under the neck of a user lying on a flat surface and between the shoulders and the head of the user and includes an expandable, but non-elastic and non-stretchable, bellows section, as well as a shoulder section, a head frame section and a head section. A hand operated air pump with an air pressure relief valve is connected to the bellows section for manually filling the bellows section and for expanding and contracting the bellows section thereby to cause distraction of the vertebrae (to stretch the neck, in common parlance) and to release a stretching force on the neck. The kit includes at least two, preferably three, interchangeable head sections for accommodating substantially all human head sizes. Further, the kit includes a triangular-in-cross-section base stand for supporting the device at a small angle to the horizontal.

The kit described in the '328 patent application can be used effectively in an out-patient, e.g. a home, environment. But it relies on manual pumping of the bellows by the user and highly subjective human monitoring while pumping to achieve a desired 'feel.' Such inherently is prone to human error and/or whim. It is thus neither as repeatable nor as consistent in the long term as desired.

BRIEF DESCRIPTION OF THE DRAWINGS

FIG. 13A illustrates a static regimen, FIG. 13B illustrates a ramped regimen, and FIG. 13C illustrates a ramped and cycled or intermittent regimen.

DESCRIPTION OF THE PREFERRED EMBODIMENTS OF THE INVENTION

According to the '328 patent application there is provided a cervical traction/stretch device kit comprising a cervical traction/stretch device including an expandable bellows section which is made of non-elastic and non-stretchable material. The device further includes a shoulder section which can be fixed to or made integral with the bellows section. At least two, preferably three, interchangeable head sections are provided so that substantially all human head sizes can be supported by the device. Also provided is a head frame section which is releasably assembled with one of the head sections, the bellows section and the shoulder section to provide a cervical traction/stretch device. The bellows section, the shoulder section and the head section have aligned U-shaped openings therein adapted to receive and support a user's neck. A pumping mechanism, preferably including an air pump and pressure relief structure are connected to the bellows section for pumping air into the bellows section for expanding the bellows section and for relieving or releasing air out of the bellows section. A triangular-in-cross-section base is provided in the kit for supporting the device at a small angle to the horizontal.

Figure 1:
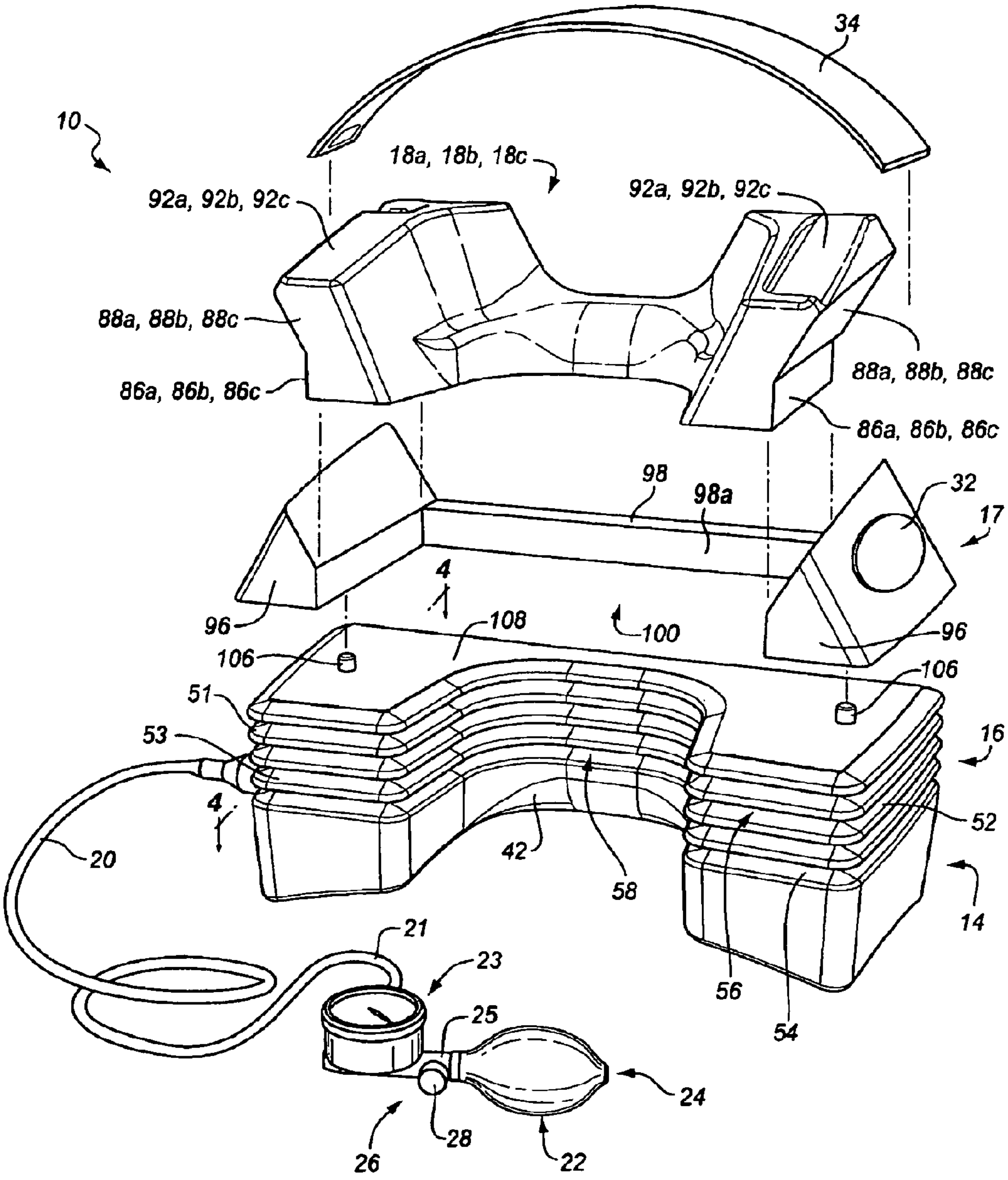
FIG. 1 is an exploded perspective front view of the cervical traction/stretch device constructed according to the teachings of the present invention.

Referring now to the drawings in greater detail, there is illustrated in FIG. 1, in an exploded perspective view, a cervical traction/stretch device 10 of a cervical traction/stretch device kit constructed according to the teachings of the present invention. The device 10 includes a shoulder section 14, a bellows section 16, a head frame section 17 and one of three head sections 18*a* (FIG. 5), 18*b* (FIG. 6) or 18*c* (FIG. 7) forming parts of the kit.

The cervical traction/stretch device 10 further includes a tubing 20 connected to the bellows section 16 or through the shoulder section 14 as shown, and having, at an outer end 21 thereof, a manual air pump 22 in the form of a manually compressible bulb 22 for pumping the cervical traction/stretch device 10 with air. A pressure gauge 23 is provided between the tubing 20 and the pump 22. The compressible bulb 22 has, at its outer end, a one way inlet valve 24 which allows air to be sucked into the bulb 22, but does not allow air to flow out of the bulb 22 when it is compressed.

Adjacent to the bulb 22 and mounted to a coupling 25 carrying the pressure gauge is a relief valve 26 which comprises a knurled thumbscrew 28. When the thumbscrew 28 is rotated into the coupling 25, no air can escape from the cervical traction/stretch device 10 and, when the thumbscrew 28 is threaded outwardly, the relief valve 26 is opened to allow compressed air to escape from the cervical traction/stretch device 10 through the tubing 20 and out of the relief valve 26.

In addition to the manually compressible bulb 22 and the tubing 20, the cervical traction/stretch device 10 includes, on either side of the head frame 17, loop and hook type fastening structure 32 of the type sold under the trademark VELCRO and the device kit further includes a head strap 34 (FIG. 8) which is adapted to be received over a user's head and secured to the head frame 17. The strap 34 has, on its inner surface thereof, a fabric texture which is adapted to attach to the fastening structures 32 on each side of the head frame 17 as will be described in greater detail hereinafter.

The shoulder section 14, the bellows section 16 and the head sections 18*a*, 18*b* or 18*c* each have various specially shaped curved surfaces for allowing the device 10 to create comfortable and therapeutic stretching to a user's neck. These specially shaped curved surfaces are described in detail in U.S. Pat. No. 5,441,781, the disclosure of which is incorporated herein by this reference.

The bellows section 16 is constructed with a plurality, e.g., four undulations 51, 52, 53, and 54 in the illustrated embodiment, and is constructed and arranged to raise and support the cervical curve of a user's neck during inflation.

Figure 3:
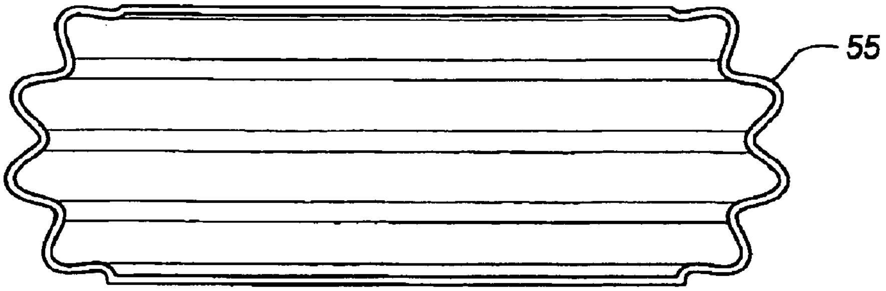
FIG. 3 PRIOR ART
FIG. 3 is a cross-sectional view through an inflated prior art bellows section of a prior art cervical traction/stretch device.

According to the teachings of the present invention, the bellows section 16, while being expandable by reason of the undulations 51-54, is made of non-elastic and non-stretchable material, preferably PVC, as opposed to a prior art elastic bellows section. This is important, since, as shown in FIG. 3, in a prior art elastic bellows 55 the material stretches laterally outwardly, sidewise, resulting in less traction or stretch force being applied on a user's neck and causes erroneous pressure readings. In this respect, the pressure gauge may be reading a constant value for the pumped air pressure going into the stretching of the prior art bellows 55, leaving the user to believe that he or she has reached a predetermined pressure value which is a maximum value for creating a maximum stretch force. In one preferred embodiment, the shoulder section and bellows section in accordance with one embodiment of the invention are made integral from P130 Plastisol having a 70-80 durometer on the Shore A scale.

Figure 4:
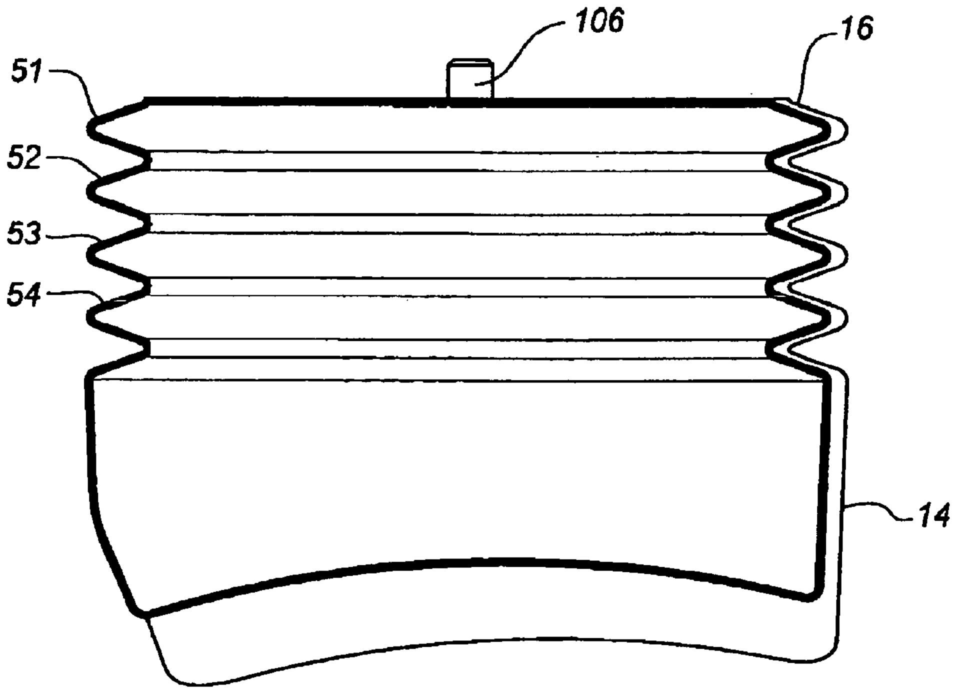
FIG. 4 is a cross-sectional view through an inflated bellows section of a cervical traction/stretch device constructed according to the teachings of the present invention.

By making the bellows section 16 with a non-elastic and non-stretching material, such as PVC, the air pressure will cause axial or longitudinal expansion of the bellows section 16, as shown in FIG. 4 but will not cause lateral or transverse bulging, deforming or stretching of the bellows section 16. Also, the actual air pressure in the bellows section 16 relative to actual stretch will be displayed on the pressure gauge 23.

Figure 2:
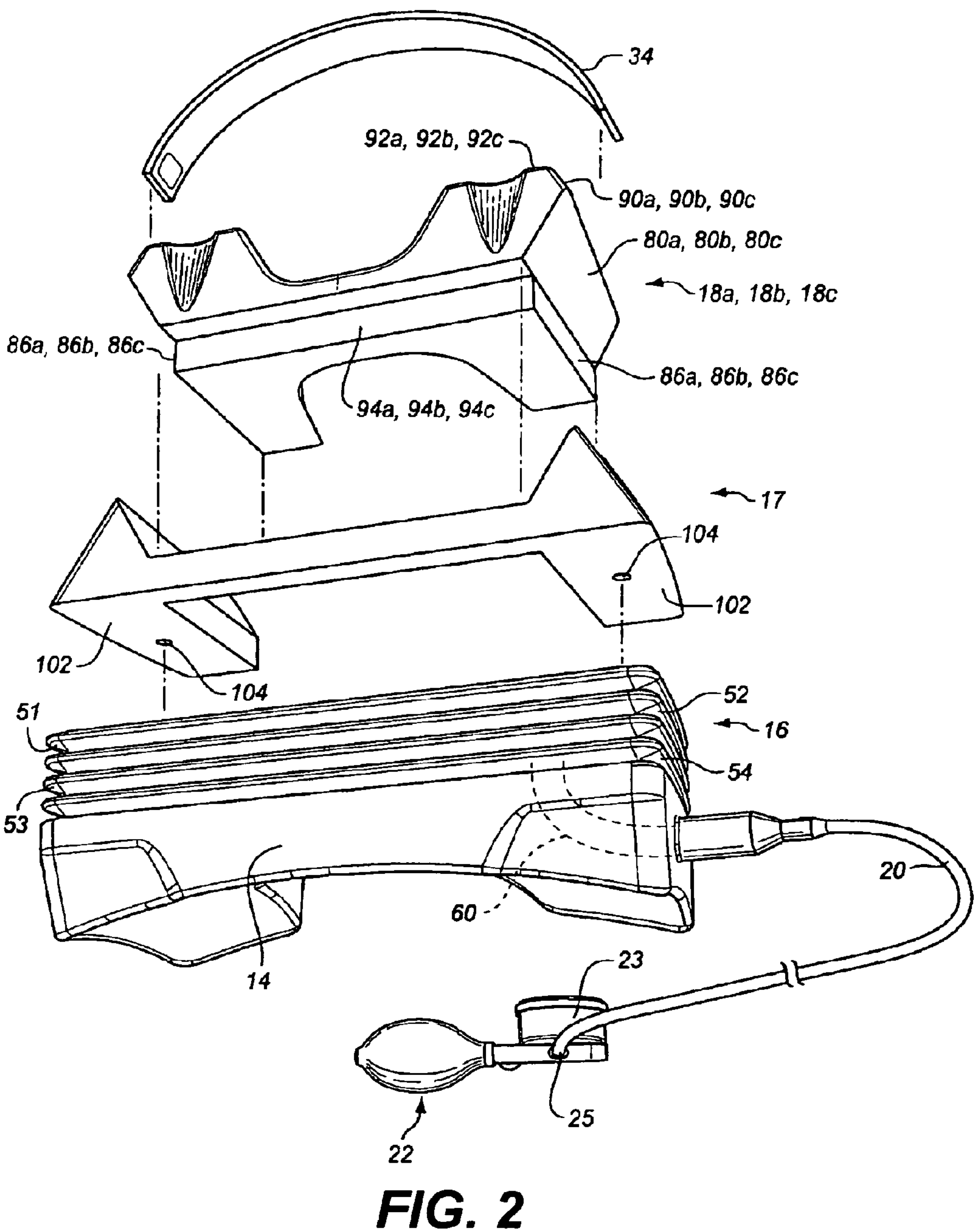
FIG. 2 is an exploded perspective rear view of the cervical traction/stretch device constructed according to the teachings of the present invention.

In the integral shoulder section 14 and bellows section 16, the shoulder section has a passage 60, shown in phantom in FIG. 2, for connecting the tubing 20 to the bellows section 16.

The bellows section 16 is generally rectangular and extends substantially the full height and width of the device 10. The bellows section 16 has a top side 56 and an arcuate, semi-circular or U-shaped surface 58 extending downwardly from the top side 56 generally aligned with a U-shaped surface 42 of the shoulder section 14 to provide a nesting support for a user's neck.

Figure 5:
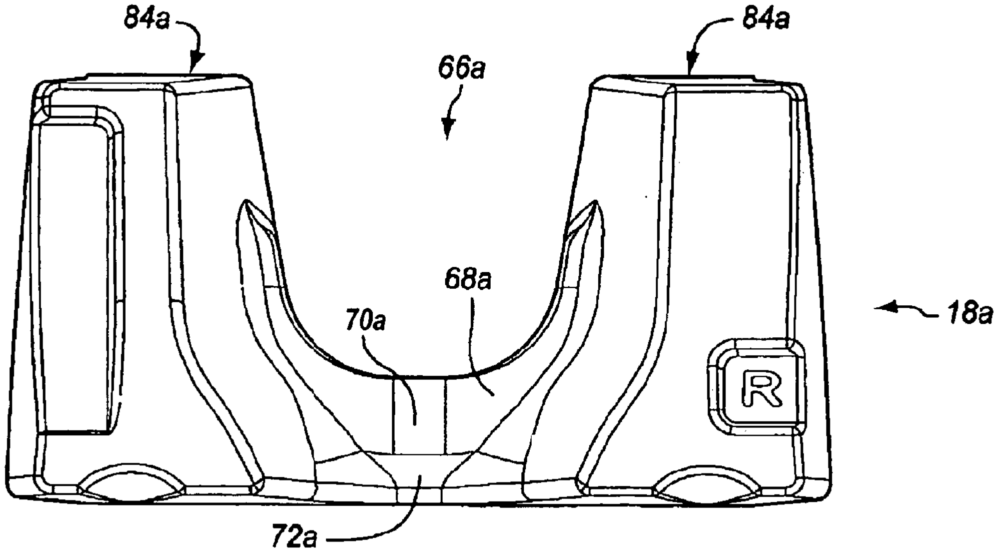
FIG. 5 is a top plan view of a regular size head section of the inflatable cervical traction/stretch device shown in FIG. 1.
Figure 6:
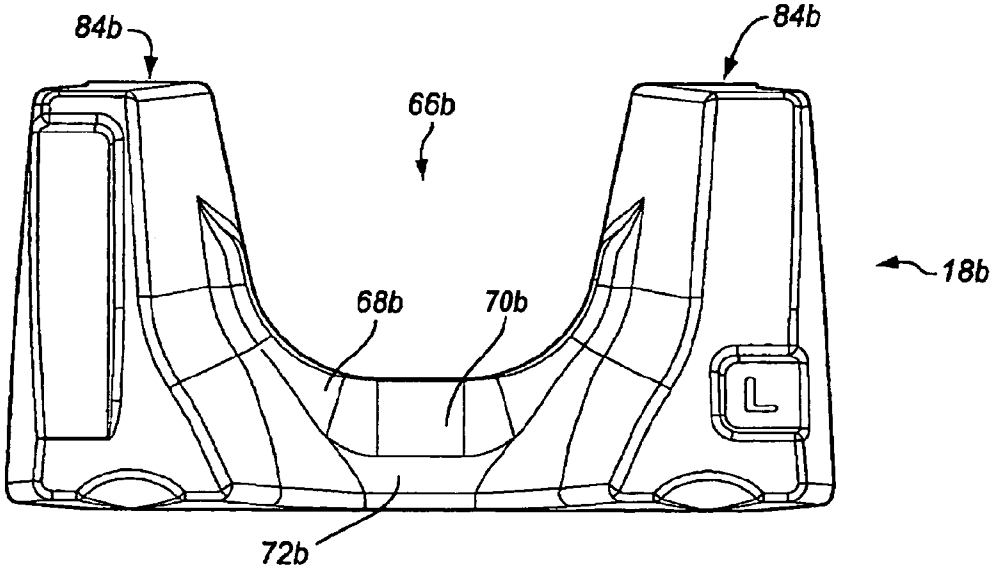
FIG. 6 is a top plan view of a large size head section of the inflatable cervical traction/stretch device shown in FIG. 1.
Figure 7:
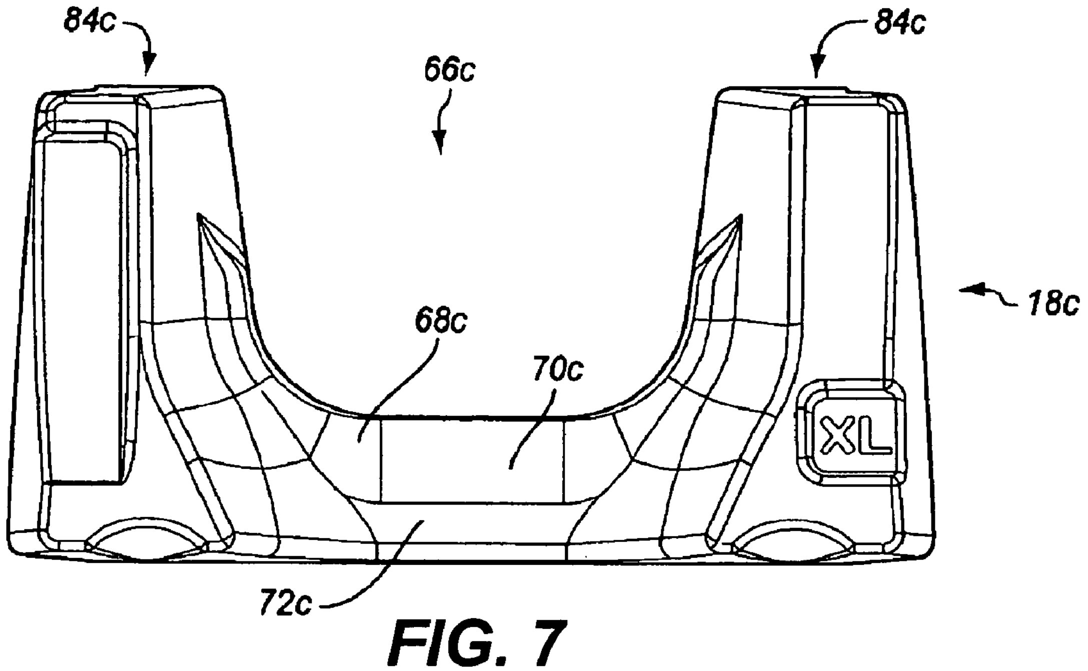
FIG. 7 is a top plan view of an extra large head section of the inflatable cervical traction/stretch device shown in FIG. 1.

A regular size head portion 18*a* is shown in FIG. 5. A large size head portion 18*b* is shown in FIG. 6. Finally, a wide size head portion 18*c* is shown in FIG. 7. In accordance with one embodiment of the invention, the head sections 18*a*, 18*b*, and 18*c* are made from polyurethane self-skinning foam. Those of skill in the art will appreciate that any suitable material alternative is contemplated as being within the spirit and scope of the invention.

Each head section 18*a*, 18*b* or 18*c* is generally rectangular in shaped and is formed with a generally U shape featuring a U-shaped opening 66*a*, 66*b* or 66*c* (for receiving the backside of a user's head) at an upper or free end thereof. Each head section also has a generally arcuate or semi-cylindrical U-shaped and inclined surface 68*a*, 68*b* or 68*c* having similar surface portions 70*a*, 70*b* or 70*c* (see FIGS. 5, 6, and 7) that inclines slightly downwardly at the center to fit the cervical curve of the user's neck. Finally, each head section also has a lower head receiving surface 72*a*, 72*b* or 72*c* having a center portion that curves downwardly for mating with the cervical curve.

The width of the U 66*b* and the U 66*c* is greater than the width of the U 66*a*. As shown in FIGS. 5, 6 and 7, the edge of the U 66*c* is less inclined in a horizontal direction than the edge of the U 66*b*. Also, the width of the portion 70*c* and the width of the surface 72*c* are less than the width of the portion

70*b* and of the surface 72*b* which in turn are less than the width of the portion 70*a* and of the surface 72*a*. These slightly different constructions of the head sections 18*a*, 18*b* or 18*c* enable them to receive and accommodate heads of different size which are labeled as follows: head section 18*a*, R for regular; head section 18*b*, L for large; and head section 18*c*, XL for extra large.

With these three head sections 18*a*, 18*b* and 18*c*, the cervical/traction device kit can fit or can accommodate substantially all human heads/necks or at least most of them.

As shown in FIG. 1 the device 10 has in the U-shaped openings and at the center of the U-shaped surfaces 42, 58 and 68*a* (FIG. 5), 68*b* (FIG. 6) or 68*c* (FIG. 7) curved straight or inclined surfaces including surfaces 68*a* (FIG. 5), 68*b* (FIG. 6) or 68*c* (FIG. 7) and 70*a* (FIG. 5), 70*b* (FIG. 6) or 70*c* (FIG. 7), for receiving the cervical curve of the neck. Then as one moves to the left side or the right side of the U-shaped openings in the area of the U-shaped opening in the head section 18*a*, 18*b* or 18*c*, the head receiving surface 72*a*, 72*b* or 72*c* has a pronounced shoulder, the occipital bone receiving surface and then a gentle sloping curving surface portion for supporting the head above the occipital bone on each side of the head. The paired surfaces 68*a* and 70*a*, 68*b* and 70*b*, and 68*c* and 70*c* are shaped to grasp the occiput and mimic two hands manually supporting the head and gently pulling the occiput away from the shoulders when the bellows are filled, thereby to optimize the grasp on the occiput and to substantially reduce or eliminate slippage.

As shown in FIGS. 5, 6 and 7, near a top side of the head section 18*a*, 18*b* or 18*c*, the U-shaped surface 68*a*, 68*b* or 68*c* slopes in a longitudinal direction downwardly and merges in or with a smooth downwardly extending curved surface portion of the head receiving surface 72*a*, 72*b* or 72*c* that extend to outer end wall surfaces 84*a*, 84*b* or 84*c* of each head section 18*a*, 18*b* or 18*c* on each side of the head receiving surface 72*a*, 72*b* or 72*c*.

Figure 8:
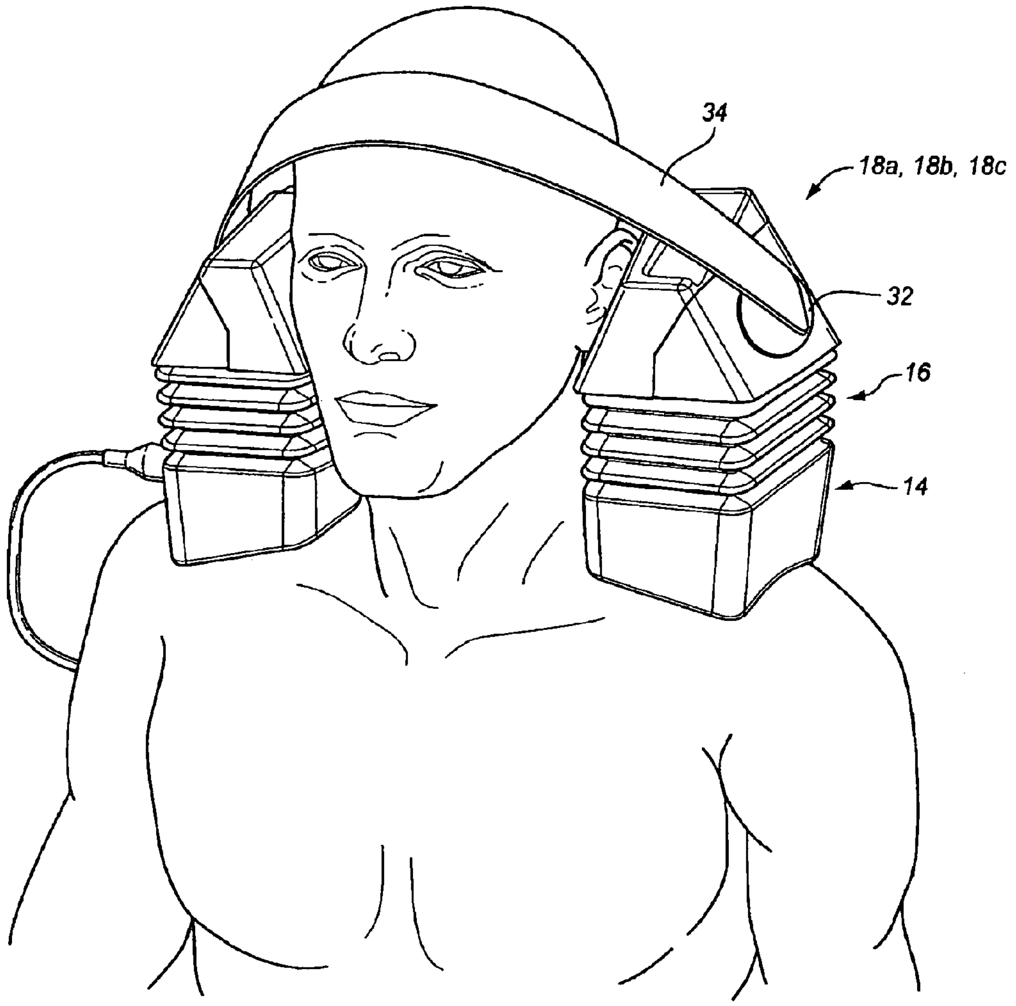
FIG. 8 is a perspective view of an upper portion of a human body lying horizontally with the head fixed in the cervical traction/stretch device of the present invention.

The ends of the head sections 18*a*, 18*b* or 18*e*, on either side of the center thereof, have left and right end wall surfaces 86*a*, 86*b* or 86*c* (FIG. 1) extending directly upwardly from a flat bottom of the head section 18*a*, 18*b* or 18*c* to an outwardly or laterally outwardly and upwardly extending inclined intermediate wall surfaces 88*a*, 88*b* or 88*c* to an inwardly inclined wall surface 90*a* (FIG. 2), 90*b* or 90*c* to an upper flat top surface 92*a*, 92*b* or 92*c*. As shown in FIGS. 6, 7 and 8 the end wall surfaces 84*a*, 84*b* or 84*c* extend downwardly to a stepped shoulder that extends inwardly to a flat, lower wall surface 94*a*, 94*b* or 94*c* (FIG. 2). All of the lower wall surfaces 86*a*, 86*b* or 86*c* and 94*a*, 94*b* or 94*c* and the intermediate wall surfaces 88*a*, 88*b* or 88*c* are constructed and arranged to fit into matching or mating surfaces of the head frame as described below.

As best shown in FIG. 1 and in FIG. 2, the head frame 17 includes two opposed and spaced apart trapezoidal and partially triangular side block portions 96 which are connected by a generally rectangular in cross section bar 98. As shown, the head frame has a U-shaped opening 100 defined by opposed, facing inner wall surfaces 98 (which mate with or abut lower wall surfaces 86*a*, 86*b* or 86*c* of each of the head sections 18*a*, 18*b* or 18*c*) and an inner wall surface 98 on the bar 98 (which mate with or abut the lower wall surfaces 94*a*, 94*b* or 94*c* of the head sections 18*a*, 18*b* or 18*c*).

The lower wall surfaces 86*a*, 86*b* or 86*c* of each of the head sections 18*a*, 18*b* or 18*c* and the lower wall surfaces 94*a*, 94*b* or 94*c* of the head sections 18*a*, 18*b* or 18*c* have identical measurements and form an identical base structure for being received in the U-shaped opening 100 and constitute an interchangeable base structure for the head sections 18*a*, 18*b* or 18*c*.

The head frame 17 has a bottom wall surface 102 having spaced apart holes 104 as shown in FIG. 2 which are adapted to releasably and frictionally receive spaced apart prongs or projections 106 on an outer surface 108 of the bellows section 16 as shown in FIG. 1.

So, in use, one of the head portions 18*a*, 18*b* or 18*c* is received and frictionally held in the head frame 17 which is fixed to the bellows section 16 by the frictional engagement of the prongs or projections 106 in the holes 104 and the thus constructed cervical traction/stretch device is laid on a flat, usually horizontal, surface ready for use by a user as shown in FIG. 8.

Figure 9:
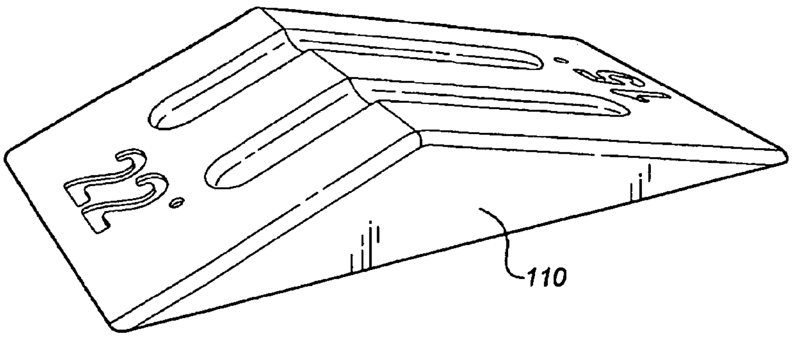
FIG. 9 is a perspective view of a triangular-cross-section base stand for supporting the cervical traction/stretch device of the present invention at a small angle to the horizontal.
Figure 10:
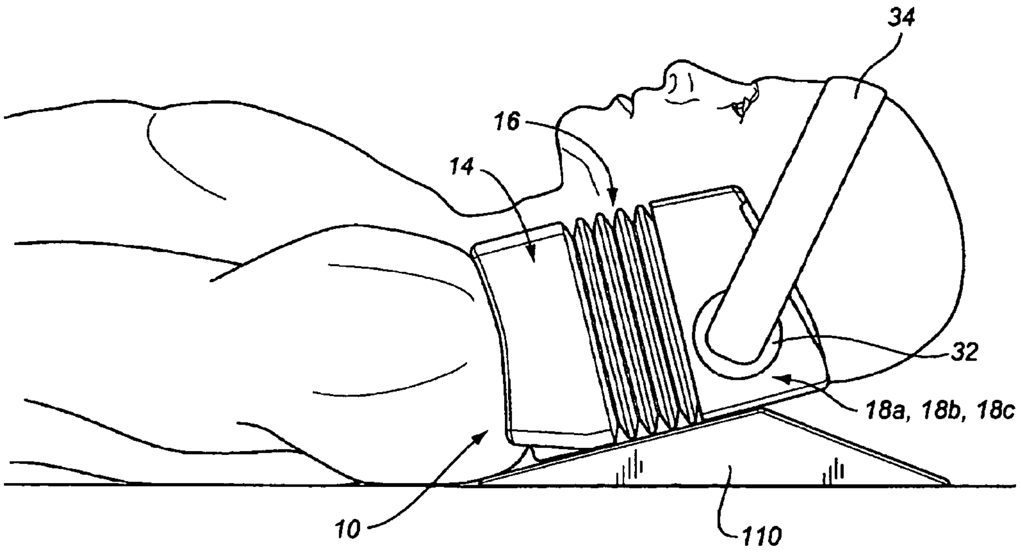
FIG. 10 is a side plan view of the cervical traction/stretch device shown in FIG. 1 positioned on base stand with the neck of a patient resting therein, placing traction on the user's neck.

It has been found that for some users, positioning of the cervical traction/stretch device at a slight angle, between approximately five and approximately thirty degrees, and preferably approximately fifteen degrees, to the horizontal provides better relief to the user by increase of the initial stretch or bend of the neck. So, the kit includes a triangular in cross section base stand 110 as shown in FIG. 9. A user using the base stand is shown in FIG. 10.

In use, the user assembles the best fitting head section 18*a*, 18*b* or 18*c* into a cervical traction/stretch device 10, lays it on the floor or on the base stand 110, fixes the head strap 34 over the temple of the head of the user, and starts pumping the hand pump/bulb 22 until a maximum pressure or level of pain relief has been reached. The user then lays there for a recommended time period to effect relief of his or her pain.

The cervical/traction device kit including three interchangeable head sections 18*a*, 18*b* and 18*c* provides a generally universally usable cervical traction/stretch device. The non-elastic and non-stretchable, but expandable, bellows section enables proper vertebral distraction at a correct pressure. Finally, the base stand 110 enables the neck to be bent slightly while using the cervical traction/stretch device to stretch the cervical portion of the neck/spine.

From the foregoing description, it will be apparent that the cervical traction/stretch device kit including the cervical traction/stretch device 10 of the present invention has a number of advantages, some of which have been described above and others of which are inherent in the invention. For example, the use of non-stretching and non-elastic material for the bellows allows the pressure in the bellows section to be gauged accurately and the three head sections provide a “universal” cervical traction/stretch device kit, one which can be used for almost every head/neck size.

Also from the foregoing description it will be apparent that modifications can be made to the cervical traction/stretch device kit and the cervical traction/stretch device 10 without departing from the teachings of the invention.

While the invented system and method described below for its use finds particular benefit in its use in a home setting where a home-patient may perform all required manual functions including equipment set-up, baseline establishment, treatment, and break-down for each session, it will also be understood that such use might instead be in the field (military); in a clinical, hospital, or hospice setting (in-patient or out-patient); in a rehabilitation center (in-patient or out-patient); and/or attended by one or more others. Thus, the term “user” intentionally broadly herein refers to any one or more of whom might operate or assist the operation of the invented system and/or implement or assist the operation of the invented method of its use on the person undergoing cervical traction treatment or therapy, as prescribed by a practicing physician. User as used herein thus is not intended in any way to limit the invention.

Figure 11:
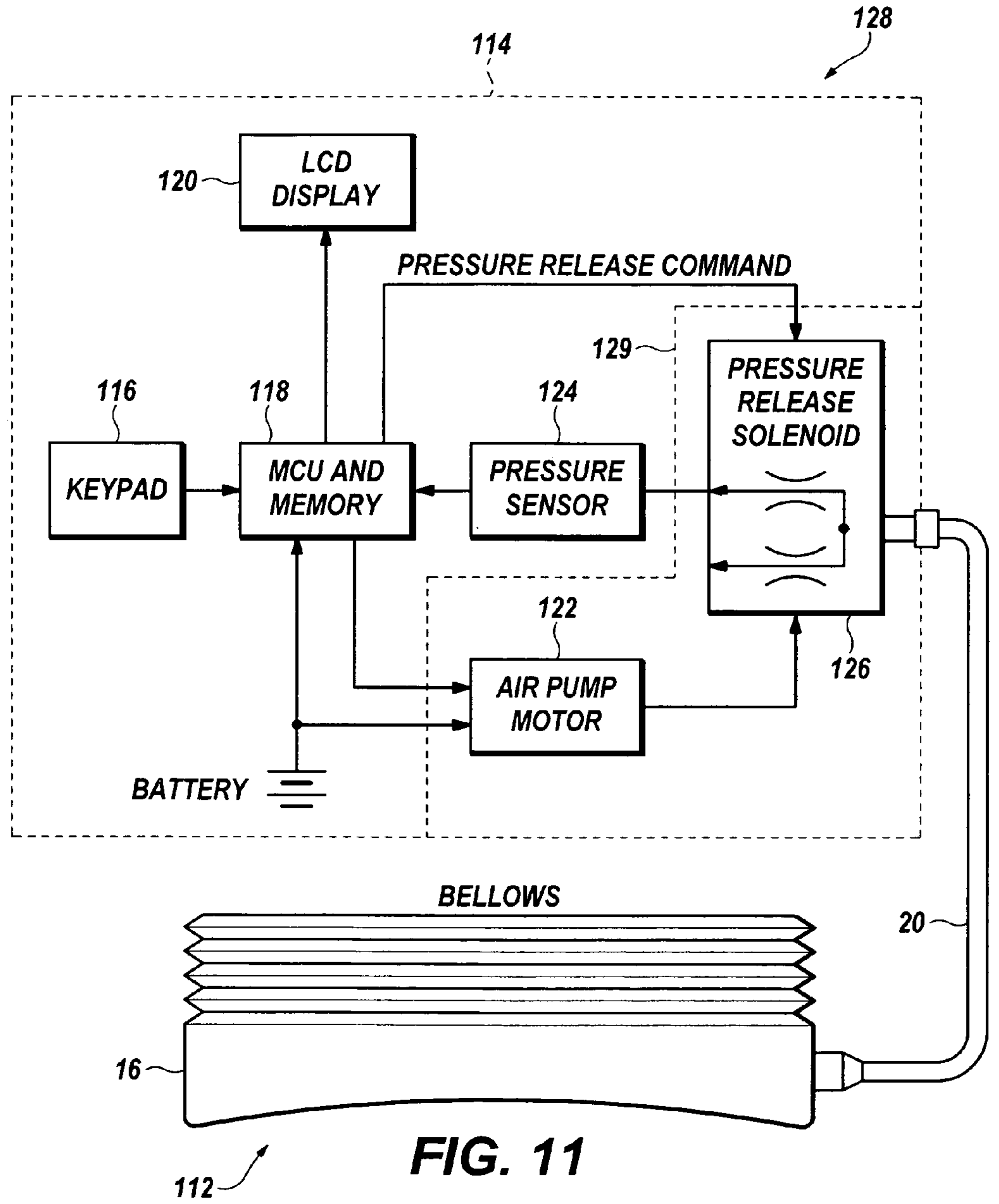
FIG. 11 is a schematic block diagram of the traction device in accordance with one embodiment of the invention.

FIG. 11 is a schematic block diagram of the traction system 112 in accordance with one embodiment of the invention. In addition to the bellows section 16 and tubing 20, system 112 includes a housing 114 containing a keypad 116, a special-purpose computer or microprocessor control unit (MCU) and memory 118, an LCD 120, an air pump/motor 122, a pressure sensor 124, and an air relief structure such as a pressure release solenoid 126. Those of skill in the art will appreciate that the bellows section 16 in conjunction with the shoulder section 14 and the head frame section 17 are referred to herein as a traction/stretch mechanism for applying tension between a user's head and shoulders. Those of skill in the art also will appreciate that the pump motor 122, the pressure sensor 124, and the pressure release solenoid 126 are referred to herein simply as a pump operatively coupled (e.g. via tubing 20) with the traction/stretch mechanism for alternately inflating and deflating the bellows section 16. Finally, those of skill will appreciate that the MCU/memory 118 operatively coupled therewith are referred to herein as an automatic or semi-automatic controller for at least semi-automatic (and, optionally, for fully automatic) control, e.g. "activation" or "deactivation" (or pressure relief) of the pump.

The controller does so by activating and deactivating the pump in such manner as to alternately and repeatably inflate and deflate the bellows to prescribed pressure levels over prescribed pressure intervals. Thus, with the bellows operatively coupled with the traction/stretch mechanism, a user undergoes at least semi-automatic traction/stretch or tension and/or relaxation of the cervical vertebrae when the traction/stretch mechanism is properly fitted to a properly positioned user. With the at least semi-automatic control of the level and duration of traction/stretch enabled by the invented system 112, user treatment and therapy is rendered more accurate, consistent, repeatable, and productive.

Those of skill in the art will appreciate that bellows pressure (and resultant user traction) is estimated (in an open-loop approach based upon the air pump motor control algorithm implemented in MCU/memory 118) rather than actually being monitored or gauged, in accordance with one embodiment of the invention. Alternatively, an electro-mechanical pressure gauge can be placed in or on a wall of the bellows so that actual pressure is monitored by the MCU/memory 118, within the spirit and scope of the invention. As another alternative, a traction or strain gauge could be placed between the user's head and shoulders or between the shoulder section 14 and the head frame section 17, so that actual user traction is monitored by the MCU/memory 118, also within the spirit and scope of the invention. Those of skill in the art will appreciate that these last two described alternatives might be described as involving closed-loop feedback approaches.

The use of the traction/stretch mechanism described and illustrated herein in which interchangeable head sections of various sized can be used, anatomical variance between various users is accommodated while providing helpful treatment to each user. Moreover, the system 112 can be used by a prone user in a home setting, e.g. in the comfort of the user's own bed.

Those of skill in the art will appreciate that the components of device 128 are typically powered by a BATTERY, as shown, the BATTERY having sufficient power to durably drive the MCU, retain the memory's contents (if volatile), and to operate the air pump motor within desired bellows pressurization parameters. Those of skill in the art will appreciate that the MCU/memory 118 and the pressure sensor 124 provide what will be referred to herein as closed-loop feedback that enables the MCU/memory 118 accurately to control the air pump motor 122 and the pressure release solenoid 126 and to ensure proper pressure levels in the bellows section 16. (Those of skill in the art will appreciate that, in accordance with one preferred embodiment of the invention, a fail-safe mode of operation of the pump motor 122 is assured whereby, in the event of battery or alternative power failure, the solenoid 126 is left in its pressure release condition to ensure patient safety and comfort in such unlikely event. Alternative fail-safe modes of operation, e.g. a manual over-ride that enables the user to safely release the tension and/or to safely remove the head-and-shoulders equipment, is contemplated also as being within the spirit and scope of the invention.) Alternative embodiments may utilize open-loop feedback, which is contemplated as being within the spirit and scope of the invention.

Those of skill in the art also will appreciate that alternative embodiments of the topology and components shown in FIG. 11 are contemplated as being within the spirit and scope of the invention. For example, two or more functions represented by separate blocks in the schematic diagram can be combined. Or a function represented by a single block in the schematic diagram can be separated into two or more functions performed by two or more components. All such alternative topologies and arrangements of components and functional blocks are contemplated as being within the spirit and scope of the invention.

As will be seen from the Examples below, a user can interact with the system in a number of useful ways to at least semi-automate his or her therapy. For example, the keypad 116 can be used by the user to enter commands to the MCU/memory 118 to communicate decisions and/or preferences regarding his or her therapy. The LCD 120 can be used by the user to ensure the decisions or preferences are comprehended, and/or to monitor the progress of the therapy as it occurs. Thus, the display is configured at least to signify the bellow's air pressure and the one or more buttons are configured to permit a user to enter at least an operational command. The memory part of the MCU/memory 118 can be used to store such decisions and/or preferences, as well as to store archival data representing previous therapy sessions and pressure level and timing interval settings. Such historical settings including nominal traction levels will be referred to herein as baseline or normative settings, and such settings can be specific to a single user or can be comprehensive of two or more users, e.g. family members. Of course, for safety purposes, in accordance with a preferred embodiment of the invention, such individual pre-set settings are accessible only by the intended family member, for example, by use, for example, of a secret code or personal identification number (PIN). This ensures that relatively short-necked user does not accidently use a relatively long-necked user's default settings.

Those of skill in the art will appreciate that such baseline pressure and interval data can be variable such that, for example, a new baseline can be recalled today from yesterday's therapy session and a new baseline can be recalled tomorrow from today's therapy session, and so on. Moreover, the memory part of the MCU/memory 118 can store longer-term therapy session data so that the same can be recalled for oversight or trend-line analysis by a prescribing physician, or can document a Medicare or Medicaid claim, or can feed a central multi-user database for universal patient care data access, retrieval, review, aggregation, academic or clinical study, or other use.

Those of skill in the art will appreciate that baseline data storage in the memory part of the MCU/memory 118 can also speed up therapy as well as rendering it more accurate, repeatable, and productive. This is because a user can simply enter a command, for example, to restore the end traction level from a previous session that the user had found therapeutic and comfortable, and the semi-automatic controller of invented system 112 can quickly operate on its own micro-controlled pump and pressure sensor sequencing to reach the previously stored pressure level. If the user particularly liked a previously recorded session, e.g. he or she found the ramp/cycle regimen (including what are referred to hereinbelow (by reference to FIGS. 13A-13C) as ramp levels/intervals, baseline levels/intervals, and modulation levels/intervals) to be particular helpful in a particular situation, the user can command the system to repeat such recorded session levels and intervals.

Figure 12:
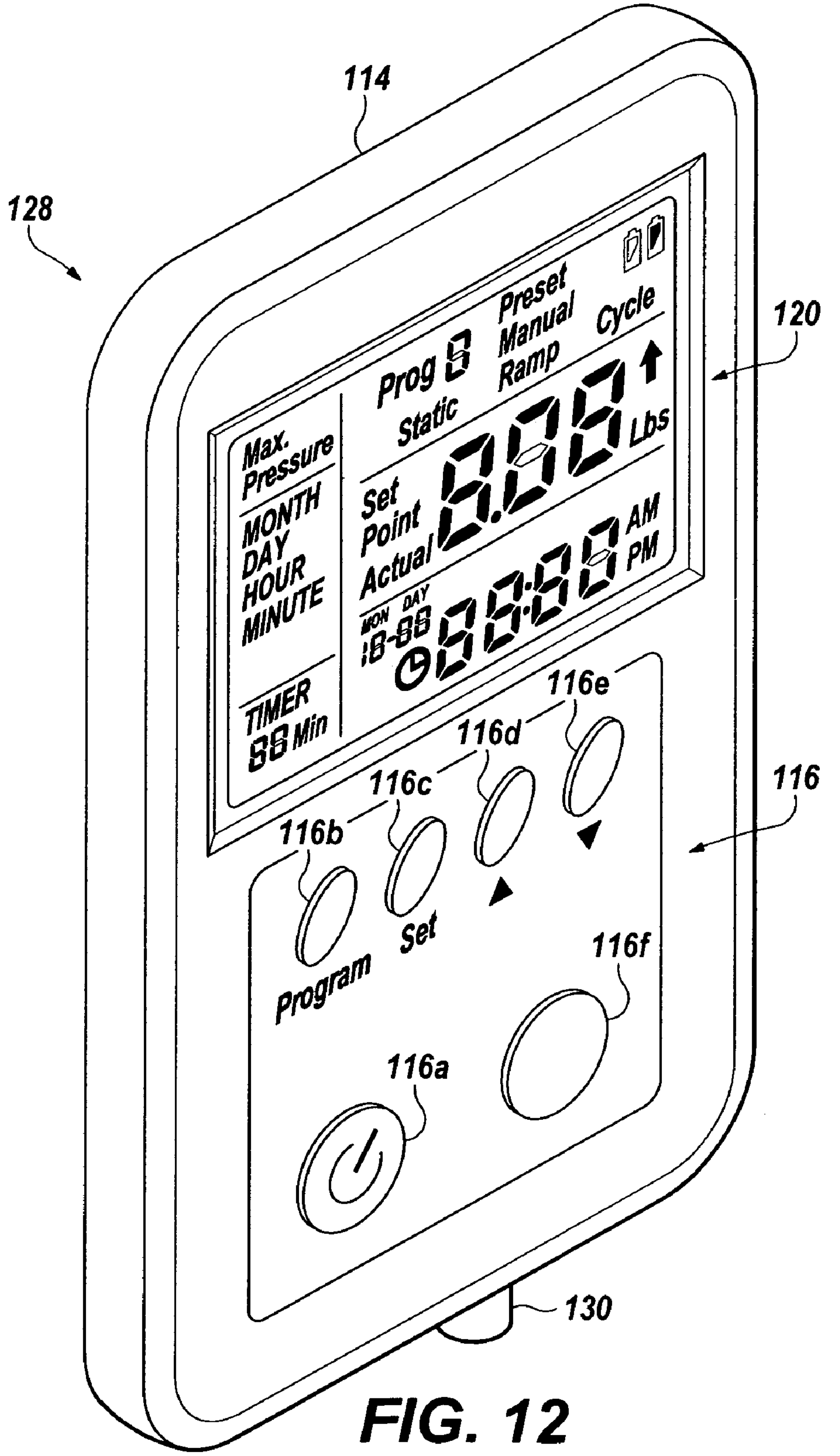
FIG. 12 is an isometric view of a hand-held, portable user interface device that permits an unattended user to control his or her own cervical traction treatment regimen with automatic or so-called 'smart-controller' computerized assistance.

FIG. 12 is an isometric view of a hand-held, portable user interface device 128 that permits an unattended user to control his or her own cervical traction treatment regimen with automatic or so-called 'smart-controller' computerized assistance. Device 128 is referred to herein as being of approximately palm size, as suggested by its resemblance in terms of form and fit to a personal digital assistant (PDA) or cellular phone such as a PRE®, I-POD®, BLACKBERRY®, or the like. In accordance with one embodiment of the invention, for example, housing 114 of device 128 can be approximately 2.0-2.5 inches in width by approximately 4-5 inches in height by approximately 0.5-1.0 inches in depth or thickness. Those of skill will appreciate that palm-sized as used herein is intentionally broad and is meant to underscore the relatively small size of the device and its fit-ability against a user's palm and within a user's grasp between thumb and cupped-and-splayed fingers of the user's hand. Thus, other dimensions, whether larger or smaller, are contemplated as being within the spirit and scope of the invention.

The keypad 116 and the LCD 120, each operatively coupled with the other via the MCU/memory 118, are referred to herein as a user interface (UI). Those of skill will appreciate that, in accordance with one embodiment of the invention, the keypad 116 includes an ON/OFF key 116*a*, a PROGRAM key 116*b*, a SET key 116*c*, a pair of UP/DOWN (or increment/decrement) keys 116*d*/116*e*, and a START/STOP key 116*f*. The LCD 120 in accordance with one embodiment of the invention includes a MAX PRESSURE indicator, a CALENDAR/CLOCK (MONTH/DAY/HOUR/MINUTE), a PROGRAM ("Prog") mode indicator, a STATIC/RAMP/CYCLE program mode indicator, a PRESET/MANUAL mode indicator, and a SET POINT/ACTUAL pressure indicator. More, fewer, different, or differently arranged keys and display regions and functions are contemplated as being within the spirit and scope of the invention.

The PROGRAM key 116*b* selects one of MANUAL, STATIC, RAMP, and CYCLE modes of operation. The SET key 116*c* is used to scroll through various parameters such as START POINT, MAX PRESSURE, MONTH, DATE, HOUR, MINUTE, and TIMER to set and save the same in memory. The UP/DOWN keys 116*d*/116E are used to adjust the selected parameter, which is indicated as selected in LCD 120 by its lighting up or flashing. When PROGRAM is in MANUAL mode, the UP/DOWN keys 116*d*/116*e* inflate/deflate the bellows section 16 to MAX PRESSURE or zero. When a desired MAX PRESSURE is reached, the user presses the SET key 116*c* and the maximum pressure is saved in memory and displayed on LCD 120 as the SET POINT. By pressing the SET key 116*c* for more than three seconds, the SET POINT will be reset and the MAX PRESSURE can be reset as above.

The CALENDAR/CLOCK is set using the SET key 116*c* in combination with the UP/DOWN keys 116*d*/116*e*, in a conventional manner. When TIMER is displayed (by pressing the SET key 116*c* until it is illuminated or flashing), treatment duration can be set by pressing the UP/DOWN keys 116*d*/116*e*. The START/STOP key 116*f* is used to start or stop the treatment based upon the selected PROGRAM.

An air pressure port 130 operatively connectable via one or more tubes such as tubing 20 is provided on an exterior edge of housing 114, as shown. The form and fit of such an air pressure port is rendered compatible with tubing 20 and, within the spirit and scope of the invention, can be implemented in any suitable manner to provide an accessible way to interconnect the bellows section 16 and the invented palm-sized device 128. In MANUAL mode, the UP/DOWN buttons 116*d*/116*e* are pressed to set initial comfort-zone traction (slight traction/stretch), and thereafter to adjust the pressure in the bellows section 16 and thus the level of traction/stretch experienced by the user.

In accordance with one embodiment of the invention, at any time during treatment in MANUAL or PROGRAM mode, pressing the ON/OFF button 116*a* (or, as described above, loss of battery or alternative power) depressurizes the bellows section and terminates treatment. Those of skill in the art will appreciate that various operational parameters (including data that may lead to a conclusion as to why treatment may have been terminated) nevertheless can be stored in the memory part of MCU/memory 118 for later review and/or use.

It will be appreciated that the automatic air pump/motor 122 is configured as BATTERY-operated dual-chamber air pump or any suitable alternative that is capable of pressurizing the bellows section 16 to the required traction forces (e.g. between approximately forty and approximately fifty pounds, which corresponds to approximately three-four pounds per square inch (3 psi-4 psi) bellows pressure) specified in the stored treatment programs in the automatic pump device's memory. (Those of skill in the art will appreciate that the MAXIMUM PRESSURE D described below by reference to FIGS. 13A-13C necessarily is equal to or less than the actual pressure capacity of the pneumatic subsystem of which the air pump/motor 122 is the main part.) The liquid crystal display (LCD) 120 screen shows the user which program he or she has selected and shows a number that indicates the approximate pressure inside the bellows section 16. This number can be used as a reference for treatment repeatability unique for each user.

Those of skill in the art will appreciate that the memory part of MCU/memory 118 is configured to store instructions, operational parameters, and archive data representative of previously prescribed levels and timing intervals relating either to manually commanded settings or programmed settings. Thus, MCU/memory 118 "memorize" the pressure/traction setting, store the setting in the memory, and, upon demand by a user, automatically activate the air pump/motor 122 to inflate the bellows section 16 to the given pressure/traction setting. Those of skill in the art also will appreciate that the display 120 is configured to display the operational status of the device and data representative of one or both of prescribed levels or timing intervals and archive data relating to previously stored or currently in-use levels and intervals.

Alternative configurations and dimensions are contemplated as being within the spirit and scope of the invention. For example, a separate pump motor and/or solenoid housing can be provided to distribute potentially larger-form-factor and more power-hungry components more wisely within the system. Such a separate housing (illustrated by dashed line 129 in FIG. 11) for a potentially larger-form-factor pump motor and/or solenoid could be connected to the palm-sized device via a wiring harness, could be connected to the bellows via a length of tubing, and could be connected to its own separate, larger-form-factor power supply. The separate power supply could be a more robust battery pack charged by alternating current (AC) line power transformed and rectified down to direct current (DC) power. Or an AC pump motor and/or solenoid could be connected directly, via appropriate isolation for safety considerations, to an AC power line. Thus, in such an alternative embodiment, a more robust air pump and/or solenoid can be provided to more quickly and effectively inflate and deflate the bellows, while leaving only a convenient, lightweight, palm-sized housing containing the UI and controller functions comfortably in the hand of the user.

Figure 13A:
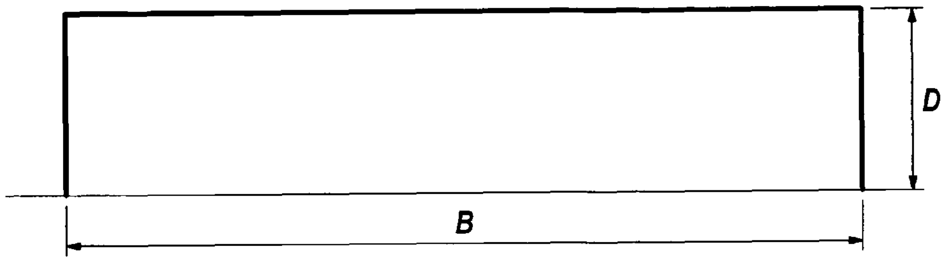
FIGS. 13A, 13B, and 13C represent exemplary traction regimens in the form of pressure versus time graphs illustrating various treatment methods in accordance with embodiments of the invention. More particularly.
Figure 13B:
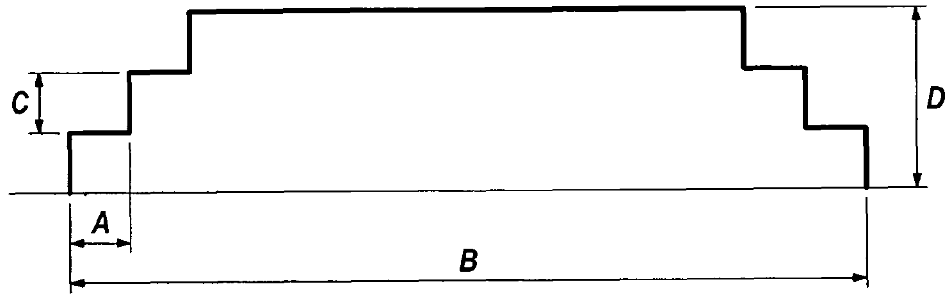
Figure 13C:
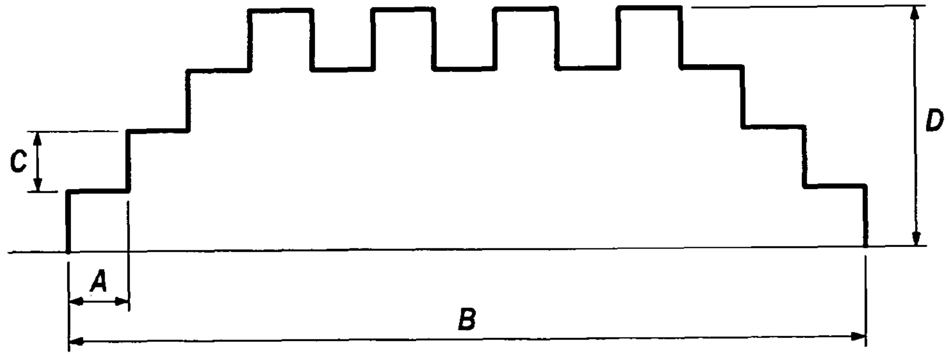

FIGS. 13A, 13B, and 13C represent three exemplary traction regimens in the form of pressure versus time graphs illustrating various treatment methods in accordance with embodiments of the invention. More particularly, FIG. 13A illustrates a static regimen, FIG. 13B illustrates a ramped regimen, and FIG. 13C illustrates a ramped and cycled (intermittent or modulated) regimen. These regimens will be described below by way of example. Those of skill in the art will appreciate that all pressures are relative to an ambient, approximately atmospheric, pressure standard representing the prevailing pressure condition in the treatment site and in the treatment equipment. Thus, pressures illustrated in FIGS. 13A, 13B, and 13C are not absolute but are relative to such an ambient pressure.

EXAMPLE 1

A user is situated in a supine position with his or her head resting on an appropriately fitting one of the three head sections 18*a*, 18*b*, or 18*c*. The user or an attendant cups the palm-sized controller device 128 in his or her hand. The user selects the a first of three programmed (stored) automatic traction regimens by pressing the PROGRAM button 116*b* and the SET button 116*c*. A so-called STATIC traction/stretch regimen illustrated in FIG. 13A automatically commences. In accordance with this static regimen, the bellows section is quickly pressurized from ambient to a defined, so-called "baseline", pressure level D in a single step, then maintained at the defined pressure level D for a defined pressure interval B, then quickly depressurized to ambient. The user can view the estimated static pressure level achieved on the LCD 120. The user alternatively can choose other regimens, depending upon how he or she initially feels on a given day or has responded to certain regimens previously.

Those of skill in the art will appreciate that the defined pressure level D and interval B are variable, and can range broadly depending upon user condition and comfort. An exemplary static pressure level typically can range upwards to approximately three or four psi corresponding to approximately forty or fifty pounds of traction. An exemplary static pressure interval can range upwards to approximately ten minutes. Those of skill in the art will appreciate that alternative static pressure levels and intervals are contemplated as being within the spirit and scope of the invention.

Those of skill also will appreciate that the MCU/memory 118 (a microcontroller operatively coupled with a memory) can record data relevant to the selected regimen and pressure and timing thereof for archival recording purposes, trend analysis, regimen modification, reporting, accounting, billing, reimbursement, and/or other purposes. Such recorded data typically would include a date, time, time-of-day 'stamp', a user name or identification (e.g. a personal identification number or PIN), etc. along with the regimen-relevant data associated with a particular traction treatment session.

Those of skill in the art will appreciate that the invented system is intuitive, easy to use, unimposing, lightweight, and portable, thus encouraging its use in an unassisted home environment where leisure and comfort rule. The automatic and programmed regimens are very consistent and highly repeatable. As such, the invention takes much of the guess work and inaccuracies out of traction/stretch treatment regimes. Recorded progress can be monitored by the user or by a remote oversight facility or person.

EXAMPLE 2

An alternative traction/stretch regimen is illustrated in FIG. 13B, which features a so-called ramp regimen. Those of skill in the art will appreciate that the treatment method steps described above apply in general, but that the user instead uses the PROGRAM button 116*b* and the SET button 116*c* to select the programmed RAMP mode of automatic operation. In accordance with this ramp regimen, the bellows section is (step-wise by a step amplitude C over a time interval A) ramped upwardly in three approximately equal increments over three approximately equal intervals from ambient to a defined pressure level D, then maintained at the defined pressure level D for a defined pressure interval, then is oppositely (step-wise) ramped downwardly (depressurized) in three approximately equal increments over three approximately equal intervals of time to ambient. The targeted baseline level is indicated by a dashed line in FIG. 13B, and can be in the range described above. The constant level can be maintained for an interval of approximately eight minutes, and the ramp up and ramp down intervals can be approximately one minute each, for a total session time of approximately ten minutes, as before.

EXAMPLE 3

An alternative traction/stretch regimen is illustrated in FIG. 13C, which features a so-called ramp-and-cycle ("Cycle") regimen. Those of skill in the art will appreciate that the treatment method steps described immediately above apply in general, but that the user instead presses the PROGRAM button 116*b* and the SET button 116*c* to select the programmed CYCLE mode of automatic operation. In accordance with this cycle regimen, the bellows section is ramped upwardly (for example, step-wise by a step amplitude C over a time interval A) in four approximately equal increments over four approximately equal intervals totaling approximately two minutes from ambient to a defined or target baseline pressure level, then cycled or modulated approximately three times therebelow (by way of what might be thought of as stress relief) by a defined amount for a defined interval of time, then is (step-wise) ramped downwardly (depressurized) in four approximately equal increments over four approximately equal intervals of time to ambient. The cycle or intermittent phase can be maintained, for example, for an interval of approximately six to eight minutes, and the ramp up and ramp down intervals can be approximately two minutes each, for example, for a total session time of approximately ten to twelve minutes, for example.

Those of skill in the art will appreciate that the pressure step amplitudes and/or the pressure step intervals can be different from those illustrated in FIGS. 13A-13C. For example, number and/or duration of the traction/stretch step intervals A, the lengths of the traction/stretch durations B, and/or the number and/or level of traction/stretch step amplitudes C, and/or the MAXIMUM PRESSURE D may be different as among the programmed regimens and may be different from those described and illustrated herein. \

For example, within the spirit and scope of the invention, the step-wise ramps and cycles can be curvilinear and/or ramped rather than square in profile. Indeed, typical ramp-up times are non-zero (the graphs of FIGS. 13A, B, and C being intentionally simplified and somewhat idealized for the sake of clarity of regimen) since it takes the air pump a minimum amount of time to achieve a given baseline pressure D above ambient within the bellows. Also, typical ramp-down times are non-zero since it takes the pressure relief solenoid (which in accordance with one embodiment of the invention is passive rather than actively drawing down or evacuating the bellows via reverse operation of the air pump) a minimum amount of time to achieve a return to ambient or so-called "release" pressure from the given baseline pressure D.

Those of skill in the art will also appreciate that more or fewer programmed regimens can be stored in memory such that the user has more or fewer programmed regimen options from which to choose. Finally, those of skill in the art will appreciate that the MCU/memory 118 may be more or less "smart". For example, it could within the spirit and scope of the invention effectively "train" itself to a particular user (identified by a PIN that would be entered in the UI via a USER selection display region and the SET and UP/DOWN scrolling keys or a numeric region of an expanded keypad) to afford the user a more individualized and thus more personalized experience, e.g. a learned treatment pattern based upon time of day, date, season, comfort level, etc.

Those of skill in the art will appreciate that FIGS. 13A, 13B, and 13C each represent only a single regimen or session and not necessarily an entire treatment, and that a typical treatment might include two or more such sessions appropriately spaced apart from one another by minutes, hours, or days, or longer intervals of time. Those of skill in the art also will appreciate that the sessions can vary over time, and that the MCU/memory 118 can automatically adjust the regimen between sessions, for example, to increase or decrease overall baseline level of program-controlled traction, whether the traction is of the static, ramp, cycle (modulation), or other type.

Thus, numerous additional and/or alternative traction/stretch regimens can be recorded in MCU/memory 118 of device 118 to be automatically invoked by user command and controlled by the at least semi-automatic controller, and any and all such additions or alternatives are contemplated as being within the spirit and scope of the invention.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

Finally, those of skill in the art will appreciate that the invented method, system and apparatus described and illustrated herein may be implemented in software, firmware or hardware, or any suitable combination thereof. Preferably, the method system and apparatus are implemented in a combination of the three, for purposes of low cost and flexibility. Thus, those of skill in the art will appreciate that embodiments of the methods and system of the invention may be implemented by a special-purpose (specifically programmed and instruction-configured) computer or microprocessor process in which instructions are executed, the instructions being stored for execution on a computer-readable medium and being executed by any suitable instruction processor.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. A cervical traction/stretch system comprising:

a traction/stretch mechanism for applying tension between a body's head and shoulders, the traction/stretch mechanism including a bellows;

a pump operatively coupled with the traction/stretch mechanism for alternately inflating and deflating the bellows; and an at least semi-automatic controller operatively coupled with the pump for at least semi-automatically controlling the pump by activating and deactivating the same in such a manner as to alternately and repeatably inflate and deflate the bellows to prescribed pressure levels over prescribed pressure intervals;

wherein the controller is configured for user-assisted semi-automatic operation by which the user manually adjusts the traction to a given level within a desired comfort zone and by which the controller memorizes the given level, stores the given level in a memory, and, on demand, automatically activates the pump to inflate the bellows to reproduce the given traction level.

2. The system of claim 1, wherein the controller includes a special-purpose computer having a processor and a memory operatively coupled thereto, the memory being configured to store instructions for execution by the processor and also to store the prescribed pressure levels over the prescribed pressure intervals.

3. The system of claim 2, wherein the memory is configured further to store archive data representative of the previously prescribed levels and previously prescribed timing intervals.

4. The system of claim 3 which further comprises:

a display operatively coupled with the controller, the display being configured to display data representative of an operational status of the device, wherein the display further is configured to display data representative of at least one of the prescribed levels and the prescribed timing intervals and the archive data.

5. The system of claim 1 which further comprises:

a display operatively coupled with the controller, the display being configured to display data representative of an operational status of the device.

6. The system of claim 5, wherein the display further is for displaying data representative of at least one of the prescribed levels and the prescribed timing intervals.

7. The system of claim 1, wherein the controller is configured for fully automatic operation.

8. The system of claim 1, wherein the bellows section includes a plurality of undulations and is made of non-elastic and non-stretchable material.

9. The system of claim 8, wherein the pump is operated automatically by the controller.

10. The system of claim 8, wherein the pump is operated semi-automatically by the controller on command from a user.

11. The method of claim 10, wherein the step (d) is performed by a special-purpose computer operatively coupled with one or more of the pump and the bellows.

12. The method of claim 10, after the steps (a)-(d), further comprising:

(e) automatically recalling from the memory and restoring to the bellows the recorded baseline level at a later time.

13. The method of claim 12, after the step (e), further comprising:

(f) automatically modulating the pressure supplied to the bellows to apply a predefined amount of modulating traction to the user.

14. The method of claim 13, further comprising:

(g) automatically ramping up the pressure supplied to the bellows to a nominal level and thereafter performing the modulating and thereafter automatically ramping down the pressure supplied to the bellows.

15. The method of claim 13, after the step (f), further comprising:

(g) automatically adjusting the modulating between user sessions in a predefined manner.

16. The method of claim 15, wherein the step (g) increases the overall traction realized by the user over time.

17. The method of claim 15, wherein the step (g) decreases the overall traction realized by the user over time.

18. The method of claim 15, after the step (g), further comprising:

(h) storing in the memory data representative of the prescribed pressure levels over the prescribed pressure intervals for archival purposes.

19. The method of claim 18, wherein the step (h) includes storing in the memory such data representative of plural users, each user identified by a personal identification number (PIN) also stored in the memory.

20. A cervical traction treatment method comprising:

(a) providing a cervical traction device including a manual pump for pressurizing a bellows associated with a collar, the bellows configured to alternately extend and contract the space between a user's head and shoulders;

(b) positioning the user with the device in place in a supine position;

(c) manually alternately pumping and releasing the bellows to establish a baseline level of traction between the user's head and shoulders; and (d) automatically recording the baseline level in a memory.

21. A cervical traction/stretch device comprising:

an expandable bellows section made of non-elastic and non-stretchable material; at least two head sections for accommodating different sized human heads and having an identical base; a head frame having receiving structure for receiving one of the at least two head sections at a time and having mating engaging structure for frictionally and releasably attaching to the bellows section;

a shoulder section fixed to or made integral with the bellows section; and a semi-automatic pumping mechanism for alternately expanding and contracting the bellows section, the mechanism alternately expanding and contracting the bellows section automatically upon receipt of a command from a user, wherein the at least two head sections, the bellows section, and the shoulder section each include a U-shaped opening therein adapted to receive and support a user's neck, the U-shaped openings being aligned when one of the at least two head sections is attached to the bellows section.

22. The cervical traction/stretch device of claim 21, wherein the semi-automatic pumping mechanism includes a battery-operable air pump and a battery-operable air relief structure coupled to the bellows section for pumping air into the bellows section and for relieving or releasing air out of the bellows section.

23. The cervical traction/stretch device of claim 21, wherein the semi-automatic pumping mechanism includes a line-powered air pump and a line-powered air relief structure coupled to the bellows section for pumping air into the bellows section and for relieving or releasing air out of the bellows section.

24. The cervical traction/stretch device of claim 21 further comprising:

a base that is triangular in cross section for supporting the cervical traction/stretch device at a small angle to the horizontal.

25. The cervical traction/stretch device of claim 24, wherein the base includes at least one side for supporting the cervical traction/stretch device, and wherein said angle of the at least one side is between approximately five degrees and approximately thirty degrees to the horizontal.

26. The cervical traction/stretch device of claim 21, wherein the bellows section includes a plurality of undulations.

27. The cervical traction/stretch device of claim 21, wherein at least a first head section, a second head section, and a third head section are provided.

28. The cervical traction/stretch device of claim 27, wherein each head section has head receiving surfaces surrounding the U-shaped opening in each head section, wherein the U-shaped opening in the second head section has a width greater than the U-shaped opening in the first head section, and wherein the U-shaped opening in the third head section has a width greater than the U-shaped opening in the second head section.

29. The cervical traction/stretch device of claim 28, wherein the head receiving surfaces of the first head section, the second head section, and the third head section have slightly different configurations to accommodate human heads of different size.

30. The cervical traction/stretch device of claim 21 further comprising:

a strap adapted to be received over a user's head and secured to the head frame.

31. The cervical traction/stretch device of claim 21 further comprising:

a palm-sized housing containing one or more batteries, one or more buttons, a display, the semi-automatic pumping mechanism, an automatic pressure relief mechanism, a controller and a memory, the palm-sized housing providing an air pressure port operatively connectable via one or more tubes extending between the automatic pump and the expandable bellows.

32. The cervical traction/stretch device of claim 31, wherein the display is configured at least to signify the bellow's air pressure and wherein the one or more buttons are configured to permit a user to enter the command.

* * * * *